United States Patent
Weiner et al.

(10) Patent No.: US 8,658,843 B2
(45) Date of Patent: Feb. 25, 2014

(54) HYDROGENATION CATALYSTS PREPARED FROM POLYOXOMETALATE PRECURSORS AND PROCESS FOR USING SAME TO PRODUCE ETHANOL WHILE MINIMIZING DIETHYL ETHER FORMATION

(75) Inventors: Heiko Weiner, Pasadena, TX (US); Zhenhua Zhou, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 156 days.

(21) Appl. No.: 13/419,617

(22) Filed: Mar. 14, 2012

(65) Prior Publication Data
US 2013/0245337 A1 Sep. 19, 2013

Related U.S. Application Data

(63) Continuation-in-part of application No. 13/267,149, filed on Oct. 6, 2011, now Pat. No. 8,536,382.

(60) Provisional application No. 61/583,874, filed on Jan. 6, 2012.

(51) Int. Cl.
*C07C 29/149* (2006.01)

(52) U.S. Cl.
USPC .......................................................... 568/885

(58) Field of Classification Search
USPC .......................................................... 568/885
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Karl et al. |
| 3,702,886 A | 11/1972 | Argauer et al. |
| 3,729,429 A | 4/1973 | Robson |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Gruffaz et al. |
| 4,317,918 A | 3/1982 | Takano et al. |
| 4,328,373 A | 5/1982 | Strojny |
| 4,337,351 A | 6/1982 | Larkins, Jr. |
| 4,374,265 A | 2/1983 | Larkins, Jr. |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,443,639 A | 4/1984 | Pesa et al. |
| 4,465,854 A | 8/1984 | Pond et al. |
| 4,471,136 A | 9/1984 | Larkins et al. |
| 4,480,115 A | 10/1984 | McGinnis |
| 4,517,391 A | 5/1985 | Schuster et al. |
| 4,521,630 A | 6/1985 | Wattimena et al. |
| 4,550,185 A | 10/1985 | Mabry et al. |
| 4,581,473 A | 4/1986 | Polichnowski et al. |
| 4,613,700 A | 9/1986 | Maki et al. |
| 4,620,050 A | 10/1986 | Cognion et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,843,170 A | 6/1989 | Isshiki et al. |
| 4,886,905 A | 12/1989 | Larkins et al. |
| 4,978,778 A | 12/1990 | Isshiki et al. |
| 4,985,572 A | 1/1991 | Kitson et al. |
| 4,990,655 A | 2/1991 | Kitson et al. |
| 5,008,235 A | 4/1991 | Wegman et al. |
| 5,061,671 A | 10/1991 | Kitson et al. |
| 5,137,861 A | 8/1992 | Shih et al. |
| 5,149,680 A | 9/1992 | Kitson et al. |
| 5,155,084 A | 10/1992 | Horn et al. |
| 5,185,308 A | 2/1993 | Bartley et al. |
| 5,238,725 A | 8/1993 | Effing et al. |
| 5,241,106 A | 8/1993 | Inoue et al. |
| 5,243,095 A | 9/1993 | Roberts et al. |
| 5,306,845 A | 4/1994 | Yokohama et al. |
| 5,350,504 A | 9/1994 | Dessau |
| 5,426,246 A | 6/1995 | Nagahara et al. |
| 5,475,144 A | 12/1995 | Watson et al. |
| 5,476,827 A | 12/1995 | Ferrero et al. |
| RE35,377 E | 11/1996 | Steinberg et al. |
| 5,585,523 A | 12/1996 | Weiguny et al. |

(Continued)

FOREIGN PATENT DOCUMENTS

| CN | 1230458 | 10/1999 |
|---|---|---|
| CN | 102228831 | 11/2011 |

(Continued)

OTHER PUBLICATIONS

International Search Report and Written Opinion mailed May 6, 2013 in corresponding International Application No. PCT/US2012/061793.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

T. Yokoyama, et al., "Carboxylic Acids and Derivatives", Fine Chemicals through Heterogenous Catalysis, pp. 370-379, 2005.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

(Continued)

*Primary Examiner* — Elvis O Price

(57) ABSTRACT

The present invention relates to hydrogenation catalysts prepared from polyoxometalate precursors. The polyoxometalate precursors introduce a support modifier to the catalyst. The catalysts are used for hydrogenating alkanoic acids and/or esters thereof to alcohols with relatively low ether formation, preferably with conversion of the ester coproduct. The catalyst may also comprise one or more active metals.

18 Claims, 4 Drawing Sheets

(56) References Cited

U.S. PATENT DOCUMENTS

| | | | |
|---|---|---|---|
| 5,691,267 A | 11/1997 | Nicolau et al. |
| 5,719,315 A | 2/1998 | Tustin et al. |
| 5,731,456 A | 3/1998 | Tustin et al. |
| 5,767,307 A | 6/1998 | Ramprasad et al. |
| 5,821,111 A | 10/1998 | Grady et al. |
| 5,849,657 A | 12/1998 | Rotgerink et al. |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,204,417 B1 | 3/2001 | Fisher et al. |
| 6,232,352 B1 | 5/2001 | Vidalin et al. |
| 6,232,504 B1 | 5/2001 | Barteau et al. |
| 6,294,703 B1 | 9/2001 | Hara et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B1 | 8/2006 | Huber et al. |
| 7,297,236 B1 | 11/2007 | Vander Griend et al. |
| 7,351,559 B2 | 4/2008 | Verser et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,572,353 B1 | 8/2009 | Vander et al. |
| 7,608,744 B1 | 10/2009 | Johnston et al. |
| 7,863,489 B2 | 1/2011 | Johnston et al. |
| 7,884,253 B2 | 2/2011 | Stites et al. |
| 7,947,746 B2 | 5/2011 | Daniel et al. |
| 8,071,389 B2 | 12/2011 | Weck et al. |
| 8,071,821 B2 | 12/2011 | Johnston et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2006/0019360 A1 | 1/2006 | Verser et al. |
| 2006/0102520 A1 | 5/2006 | Lapinski et al. |
| 2006/0127999 A1 | 6/2006 | Verser et al. |
| 2007/0106246 A1 | 5/2007 | Modesitt |
| 2007/0270511 A1 | 11/2007 | Melnichuk et al. |
| 2008/0207953 A1 | 8/2008 | Houssin et al. |
| 2009/0005588 A1 | 1/2009 | Hassan et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0221725 A1 | 9/2009 | Chorney et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0029996 A1 | 2/2010 | Danjo et al. |
| 2010/0113843 A1 | 5/2010 | Lee et al. |
| 2010/0121114 A1 | 5/2010 | Johnston |
| 2010/0168493 A1 | 7/2010 | Le Peltier et al. |
| 2010/0196789 A1 | 8/2010 | Fisher et al. |
| 2010/0197485 A1 | 8/2010 | Johnston et al. |
| 2010/0197985 A1 | 8/2010 | Johnston et al. |
| 2010/0249479 A1 | 9/2010 | Berg-Slot et al. |
| 2011/0004033 A1 | 1/2011 | Johnston et al. |
| 2011/0082322 A1 | 4/2011 | Jevtic et al. |
| 2011/0098501 A1 | 4/2011 | Johnston et al. |
| 2011/0190117 A1 | 8/2011 | Weiner et al. |
| 2011/0190547 A1 | 8/2011 | Jevtic et al. |
| 2011/0190548 A1 | 8/2011 | Jevtic et al. |

FOREIGN PATENT DOCUMENTS

| | | |
|---|---|---|
| CN | 102229520 | 11/2011 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0400904 | 5/1990 |
| EP | 0372847 | 6/1990 |
| EP | 0408528 | 7/1990 |
| EP | 0990638 | 4/2000 |
| EP | 1262234 | 12/2002 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 83/03409 | 10/1983 |
| WO | WO 2003/040037 | 5/2003 |
| WO | WO 2005/102513 | 11/2005 |
| WO | WO 2009/009322 | 1/2009 |
| WO | WO 2009/009323 | 1/2009 |
| WO | WO 2009/063176 | 5/2009 |
| WO | WO 2009/086839 | 7/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/055285 | 5/2010 |
| WO | WO 2011/053365 | 5/2011 |
| WO | WO 2011/053367 A1 | 5/2011 |

OTHER PUBLICATIONS

Santori et al.(2000). Hydrogenation of carbonylic compounds on Pt/SiO2 catalysts modified with SnBu4, Studies in Surface Science and Catalysis, 130, 2063-2068.

Rodrigues and Bueno, "Co/SiO2 catalysts for selective hydrogenation of crotonaldehyde: III. Promoting effect of zinc," Applied Catalysis A: General (2004), 257, p. 210-211.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., The formation of ketones and aldehydes from carboxylic acids, structure-activity relationship for two competitive reactions, Journal of Molecular Catalysis A: Chemical 103 Jun. 14, 1995, 175-180.

Pestman et al., Reactions of Carboxylic Acids on Oxides, Journal of Catalysis 168:255-264 (1997).

(56) References Cited

OTHER PUBLICATIONS

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Nitta, et al. "Selective hydrogenation of $\alpha\beta$-unsaturated aldehydes on cobalt—silica catalysts obtained from cobalt chrysotile," Applied Catal. (1989), 56, p. 9-22.

Liberkova, and Tourounde, "Performance of Pt/SnO2 catalyst in the gas phase hydrogenation of crotonaldehyde," J. Mol. Catal. A: Chemical (2002), 180, p. 221-230.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.

Consonni, et al. "High Performances of Pt/ZnO Catalysts in Selective Hydrogenation of Crotonaldehyde," J. Catal. (1999), 188, p. 165-175.

Ammari, et al. "An emergent catalytic material: Pt/ZnO catalyst for selective hydrogenation of crotonaldehyde," J. Catal. (2004), 221, p. 32-42.

Ammari, et al. "Selective hydrogenation of crotonaldehyde on Pt/ZnCl2/SiO2 catalysts," J. Catal. (2005), 235, p. 1-9.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

Brunauer Emmett and Teller, J. Am. Chem. Soc. 60, 309 (1938).

International Search Report and Written Opinion for PCT/US2009/004197 mailed Mar. 24, 2010.

International Search Report and Written Opinion for PCT/US2009/004195 mailed Mar. 26, 2010.

International Search Report and Written Opinion for PCT/US2010/022947 mailed Jun. 7, 2010.

International Search Report and Written Opinion for PCT/US2010/022949 mailed Jun. 7, 2010.

Invitation to Pay Fees and Partial Search Report for PCT/US2010/022950 mailed Jun. 15, 2010.

International Search Report and Written Opinion for PCT/US2010/022950 mailed Sep. 7, 2011.

International Search Report and Written Opinion for PCT/US2010/022953 mailed Jun. 7, 2010.

International Search Report and Written Opinion for PCT/US2010/054134 mailed Feb. 28, 2011.

HYDROGENATION CATALYSTS PREPARED FROM POLYOXOMETALATE PRECURSORS AND PROCESS FOR USING SAME TO PRODUCE ETHANOL WHILE MINIMIZING DIETHYL ETHER FORMATION

CROSS REFERENCE TO RELATED APPLICATIONS

This application claims priority to U.S. Provisional App. No. 61/583,874, filed on Jan. 6, 2012. This application is also a continuation-in-part of U.S. application Ser. No. 13/267,149, filed on Oct. 6, 2011, the entire contents and disclosures of which are incorporated herein by reference.

FIELD OF THE INVENTION

The present invention relates to catalysts, to processes for making hydrogenation catalysts from polyoxometalate precursors. The catalyst may be used to manufacture ethanol with very low diethyl ether formation from a feedstock comprising an alkanoic acid and/or esters thereof in the presence of the inventive catalysts.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis*, 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst.

Existing processes suffer from a variety of issues impeding commercial viability including: (i) catalysts without requisite selectivity to ethanol; (ii) catalysts without sufficient conversion of ethyl ester, a byproduct of the carboxylic acid hydrogenation; (iii) catalysts which are possibly prohibitively expensive and/or nonselective for the formation of ethanol and that produce undesirable by-products; (iv) required operating temperatures and pressures which are excessive; (v) insufficient catalyst life; and/or (vi) the formation of significant amounts of diethyl ether, a byproduct of the carboxylic acid hydrogenation.

SUMMARY OF THE INVENTION

In one embodiment, the invention comprises a process for producing ethanol comprising the steps of: passing a gaseous stream comprising hydrogen and an alkanoic acid in the vapor phase over a hydrogenation catalyst to form a product comprising an alcohol and less than about 0.25% ether based on the total weight of the product, wherein the hydrogenation catalyst is produced by the process comprising the steps of impregnating a support modifier from ammonium metatungstate, ammonium heptamolybdate tetrahydrate, silicotungstic acid hydrate, phosphotungstic acid, silicomolybdic acid, phosphomolybdic acid, niobium oxalate hexahydrate, or vanadium oxide on a support to form a first impregnated support; calcining the first impregnated support to form a calcined support; impregnating one or more active metals from one or more metal precursors on the calcined support to form a second impregnated support, wherein the one or more active metals are selected from the group consisting of iron, cobalt, nickel, ruthenium, rhodium, platinum, palladium, osmium, iridium, titanium, zinc, chromium, molybdenum, tungsten, tin, lanthanum, cerium, manganese, and gold; and calcining the second impregnated support to form the catalyst. Especially preferred support modifiers include ammonium heptamolybdate tetrahydrate, silicomolybdic acid, phosphomolybdic acid, and vanadium oxide. In one embodiment, the alkanoic acid is acetic acid. In other embodiments, the conversion of acetic acid to ethanol is at least about 80% and the selectivity to ethanol is at least about 70%.

BRIEF DESCRIPTION OF THE DRAWINGS

The present invention will be better understood in view of the appended non-limiting figures, in which.

DETAILED DESCRIPTION OF THE INVENTION

Figure 1:
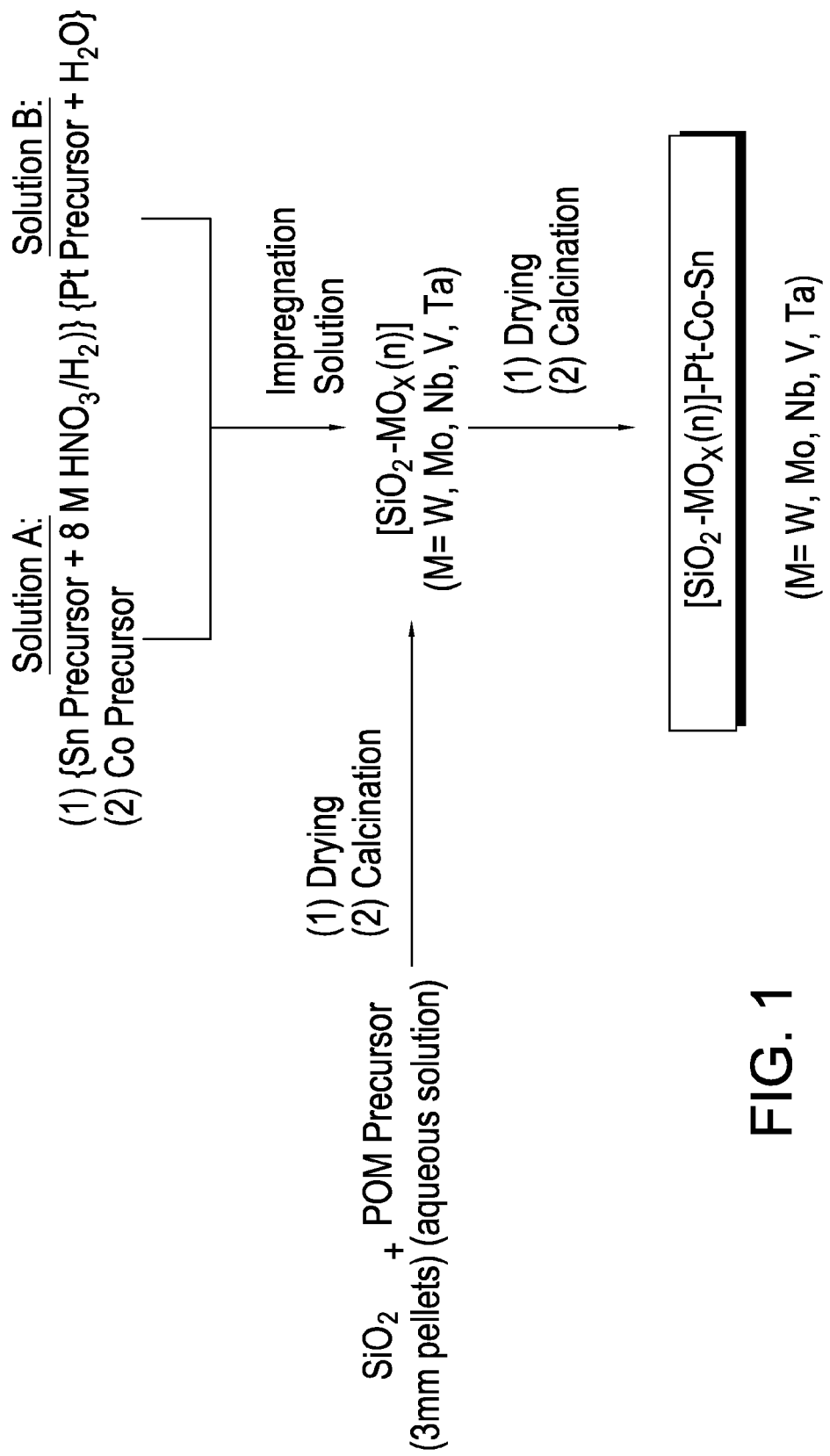
FIG. 1 provides a non-limiting flow diagram for a process for forming a catalyst according to one embodiment of the present invention.

The present invention is directed to a hydrogenation catalyst prepared using a polyoxometalate precursor. The polyoxometalate introduces one or more support modifiers onto the support. The catalysts preferably also comprise one or more active metals on a support.

The catalyst is particular suited to catalyzing the hydrogenation of an alkanoic acid, e.g., acetic acid, and/or esters thereof, e.g., ethyl acetate, to the corresponding alcohol, e.g., ethanol. When acetic acid is hydrogenated in the presence of a catalyst having acidic sites, diethyl ether byproduct is also produced. Acidic sites may be useful for increasing acetic acid conversion and ethanol selectivity. The ether byproduct needs to be purged because the diethyl ether is not converted when recycled. The purge of diethyl ether represents a loss of ethanol efficiency. Thus, the formation of the diethyl ether byproduct should be minimized or eliminated using a catalyst with acidic sites. Producing a catalyst from a polyoxometalate introduces a support modifier on a support that provides a catalyst having acidic sites that also minimizes ether formation. On a per pass basis, the selectivity to diethyl ether may be less than 0.25%, e.g., less than 0.2%, less than 0.1%, or less than 0.05%. In an exemplary embodiment, the catalyst produces substantially no diethyl ether when catalyzing an acetic acid hydrogenation. In one embodiment, the inventive catalyst comprises one or more active metals on a modified support. Preferably the modified support comprises support particles and a support modifier comprising a metal selected from tungsten, molybdenum, vanadium, niobium, chromium, and tantalum. In most embodiments, the support modifier is present as an oxide. One or more different oxides of each metal or mixtures of metals may be used as the support modifier. As discussed herein, the support modifier is added to the support from a polyoxometalate precursor.

One or more active metals may be impregnated on the support. In one embodiment, the one or more active metals are selected from the group consisting of copper, calcium, barium, magnesium, strontium, iron, cobalt, nickel, ruthenium, rhodium, platinum, palladium, osmium, iridium, titanium, zinc, chromium, molybdenum, tungsten, tin, lanthanum, cerium, manganese, and gold. In a preferred embodiment, the one or more active metals are selected from the group consisting of platinum, palladium, nickel, cobalt, copper, and tin. The total weight of all the active metals present in the catalyst preferably is from 0.1 to 25 wt. %, e.g., from 0.1 to 15 wt. %, or from 0.1 wt. % to 10 wt. %. For purposes of the present specification, unless otherwise indicated, weight percent is based on the total weight of the catalyst including metal and support.

In some embodiments, the catalyst contains at least two active metals in addition to a precious metal. The two active metals may be selected from any of the active metals identified above, so long as they are not the same as the precious metal or each other. Preferably those metals are combinations of copper, iron, cobalt, and tin. Cobalt and tin is exemplary of a catalyst for converting alkanoic acid and esters thereof to ethanol. Precious metals may be selected from the group consisting of nickel, ruthenium, rhodium, platinum, palladium, osmium, iridium, and gold. The precious metal may be in elemental form or in molecular form, e.g., an oxide of the precious metal. The catalyst may comprise the precious metal in an amount from 0.05 to 10 wt. %, e.g. from 0.1 to 5 wt. %, or from 0.1 to 3 wt. %, based on the total weight of the catalyst. It is preferred that the catalyst comprises such precious metals in an amount less than 5 wt. %, e.g., less than 3 wt. %, or less than 1.5 wt. %.

In another embodiment, the catalyst may comprise two active metals or three active metals. The first metal or oxides thereof may be selected from the group consisting of cobalt, rhodium, ruthenium, platinum, palladium, osmium, iridium and gold. The second metal or oxides thereof may be selected from the group consisting of copper, iron, tin, cobalt, nickel, zinc, and molybdenum. The third metal or oxides thereof, if present, may be selected from the group consisting of copper, molybdenum, tin, chromium, iron, cobalt, vanadium, palladium, platinum, lanthanum, cerium, manganese, ruthenium, gold, and nickel. Preferably, the third metal is different than the first metal and the second metal. In addition, the first metal and the second metal may be different, and the third metal and the second metal may be different.

The metal loadings of the first, second, and optionally third metals are as follows. The first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 8 wt. %. If the catalyst further comprises a third active metal, the third active metal may be present in an amount from 0.05 to 20 wt. %, e.g., from 0.05 to 10 wt. %, or from 0.5 to 8 wt. %. The active metals may be alloyed with one another or may comprise a non-alloyed metal solution, a metal mixture or be present as one or more metal oxides. For purposes of the present specification, unless otherwise indicated, weight percent is based on the total weight the catalyst including metal and support.

Bimetallic catalysts for some exemplary catalyst compositions, excluding cesium and tungsten on the support, include platinum/tin, platinum/ruthenium, platinum/cobalt, platinum/nickel, palladium/ruthenium, palladium/cobalt, palladium/copper, palladium/nickel, ruthenium/cobalt, gold/palladium, ruthenium/iron, rhodium/iron, rhodium/cobalt, rhodium/nickel, cobalt/tin, and rhodium/tin. More preferred bimetallic catalysts include platinum/tin, platinum/cobalt, platinum/nickel, palladium/cobalt, palladium/copper, palladium/nickel, ruthenium/cobalt, ruthenium/iron, rhodium/iron, rhodium/cobalt, rhodium/nickel, cobalt/tin, and rhodium/tin.

In some embodiments, the catalyst may be a tertiary catalyst that comprises three active metals on a support. Exemplary tertiary catalysts, excluding cesium and tungsten on the support, may include palladium/cobalt/tin, platinum/tin/palladium, platinum/tin/rhodium, platinum/tin/gold, platinum/tin/iridium, platinum/tin/cobalt, platinum/tin/chromium, platinum/tin/copper, platinum/tin/zinc, platinum/tin/nickel, rhodium/nickel/tin, rhodium/cobalt/tin and rhodium/iron/tin. More preferably, a tertiary catalyst comprises three active metals may include palladium/cobalt/tin, platinum/tin/palladium, platinum/cobalt/tin, platinum/tin/chromium, platinum/tin/copper, platinum/tin/nickel, rhodium/nickel/tin, rhodium/cobalt/tin and rhodium/iron/tin.

The preferred metal ratios may vary somewhat depending on the active metals used in the catalyst. In some embodiments, the mole ratio of the first active metal to the second active metal preferably is from 20:1 to 1:20, e.g., from 15:1 to 1:15, from 12:1 to 1:12.

In embodiments where the one or more active metals, e.g., one or more of the first, second or third metals, are applied to the catalyst sequentially, i.e., in multiple impregnation steps, the catalyst may be said to comprise a plurality of "theoretical layers." For example, where a first metal is impregnated onto a support followed by impregnation of a second metal, the resulting catalyst may be said to have a first theoretical layer comprising the first metal and a second theoretical layer comprising the second metal. As discussed above, in some aspects, more than one active metal precursor may be co-impregnated onto the support in a singles step such that a theoretical layer may comprise more than one metal or metal oxide. In another aspect, the same metal precursor may be impregnated in multiple sequential impregnation steps leading to the formation of multiple theoretical layers containing the same metal or metal oxide. In this context, notwithstanding the use of the term "layers," it will be appreciated by those skilled in the art that multiple layers may or may not be formed on the catalyst support depending, for example, on the conditions employed in catalyst formation, on the amount of metal used in each step and on the specific metals employed.

It has now been discovered that such catalysts are particularly effective as multifunctional hydrogenation catalysts capable of converting both alkanoic acids, such as acetic acid, and esters thereof, e.g., ethyl acetate, to their corresponding alcohol(s), e.g., ethanol, under hydrogenation conditions.

Support Materials

The catalysts of the present invention may be on any suitable support material preferably a modified support material. In one embodiment, the support material may be an inorganic oxide. In one embodiment, the support material may be selected from the group consisting of silica, alumina, titania, silica/alumina, calcium metasilicate, pyrogenic silica, high purity silica, zirconia, carbon (e.g., carbon black or activated carbon), zeolites and mixtures thereof. Preferably, the support material comprises silica. In preferred embodiments, the support material is present in an amount from 25 wt. % to 99 wt. %, e.g., from 30 wt. % to 98 wt. % or from 35 wt. % to 95 wt. %, based on the total weight of the catalyst.

In preferred embodiments, the support material comprises a silicaceous support material, e.g., silica, having a surface area of at least 50 $m^2/g$, e.g., at least 100 $m^2/g$, at least 150 $m^2/g$, at least 200 $m^2/g$ or at least 250 $m^2/g$. In terms of ranges, the silicaceous support material preferably has a surface area from 50 to 600 $m^2/g$, e.g., from 100 to 500 $m^2/g$ or from 100 to 300 $m^2/g$. High surface area silica, as used throughout the application, refers to silica having a surface area of at least 250 $m^2/g$. For purposes of the present specification, surface area refers to BET nitrogen surface area, meaning the surface area as determined by ASTM D6556-04, the entirety of which is incorporated herein by reference.

The preferred silicaceous support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 $cm^3/g$, e.g., from 0.7 to 1.5 $cm^3/g$ or from 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support material preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the precious metal and the one or more active metals that are disposed on the support are generally in the form of very small metal (or metal oxide) particles or crystallites relative to the size of the support, these metals should not substantially impact the size of the overall catalyst particles. Thus, the above particle sizes generally apply to both the size of the support as well as to the final catalyst particles, although the catalyst particles are preferably processed to form much larger catalyst particles, e.g., extruded to form catalyst pellets.

A preferred silica support material is SS61138 High Surface Area (HSA) Silica Catalyst Carrier from Saint-Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$.

A preferred silica/alumina support material is KA-160 (Süd Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

Support Modifiers

The support material preferably comprises a support modifier that is added to the support material using a polyoxometalate precursor. A support modifier may adjust the acidity of the support material. In another embodiment, the support modifier may be a basic modifier that has a low volatility or no volatility. In one embodiment, the support modifiers are present in an amount from 0.1 wt. % to 50 wt. %, e.g., from 0.2 wt. % to 25 wt. %, from 0.5 wt. % to 15 wt. %, or from 1 wt. % to 12 wt. %, based on the total weight of the catalyst.

As indicated, the support modifiers may adjust the acidity of the support. For example, the acid sites, e.g., Brønsted acid sites or Lewis acid sites, on the support material may be adjusted by the support modifier to favor selectivity to ethanol during the hydrogenation of acetic acid and/or esters thereof. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In general, the surface acidity of the support may be adjusted based on the composition of the feed stream being sent to the hydrogenation process in order to maximize alcohol production, e.g., ethanol production.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include those selected from the group consisting of $WO_3$, $MoO_3$, $Fe_2O_3$, $Cr_2O_3$, $V_2O_5$, $MnO_2$, $CuO$, $Co_2O_3$, $P_2O_5$, and $P_4O_{10}$ and $Bi_2O_3$. It has now surprisingly and unexpectedly been discovered that the use of such metal oxide support modifiers in combination with a precious metal and one or more active metals may result in catalysts having multifunctionality, and which may be suitable for converting an alkanoic acid, such as acetic acid, as well as corresponding esters thereof, e.g., ethyl acetate, to one or more hydrogenation products, such as ethanol, under hydrogenation conditions.

In some embodiments, the acidic support modifier comprises a mixed metal oxide comprising at least one of the active metals and an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, copper tungstate, iron tungstate, zirconium tungstate, manganese tungstate, cobalt molybdate, copper molybdate, iron molybdate, zirconium molybdate, manganese molybdate, cobalt vanadate, copper vanadate, iron vanadate, zirconium vanadate, manganese vanadate, cobalt niobate, copper niobate, iron niobate, zirconium niobate, manganese niobate, cobalt tantalate, copper tantalate, iron tantalate, zirconium tantalate, and manganese tantalate. It has now been discovered that catalysts containing such mixed metal support modifiers may provide the desired degree of multifunctionality at increased conversion, e.g., increased ester conversion, and with reduced byproduct formation, e.g., reduced diethyl ether formation.

In one embodiment, the catalyst comprises from 0.25 to 1.25 wt. % platinum, from 1 to 10 wt. % cobalt, and from 1 to 10 wt. % tin on a silica or a silica-alumina support material. The support material may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 5 to 15 wt. %.

In some embodiments, the modified support comprises one or more active metals in addition to one or more acidic modifiers. The modified support may, for example, comprise one or more active metals selected from copper, iron, cobalt, vanadium, nickel, titanium, zinc, chromium, molybdenum, tungsten, tin, lanthanum, cerium, and manganese. For example, the support may comprise an active metal, preferably not a precious metal, and an acidic or basic support modifier. Preferably, the support modifier comprises a support modifier metal selected from the group consisting of tungsten, molybdenum, vanadium, niobium, and tantalum. In this aspect, the final catalyst composition comprises a precious metal, and one or more active metals disposed on the modified support. In a preferred embodiment, at least one of the active metals in the modified support is the same as at least one of the active metals disposed on the support. For example, the catalyst may comprise a support modified with cobalt, tin and tungsten (optionally as $WO_3$ and/or as cobalt tungstate). In this example, the catalyst further comprises a precious metal, e.g., palladium, platinum or rhodium, and at least one active metal, e.g., cobalt and/or tin, disposed on the modified support.

Processes for Making the Catalyst

The present invention also relates to processes for making the catalyst. Without being bound by theory, the process for making the catalyst may improve one or more of acetic acid conversion, ester conversion, ethanol selectivity and overall productivity. In one embodiment, the support is modified with one or more support modifiers and the resulting modified support is subsequently impregnated with a precious metal and one or more active metals to form the catalyst composition. For example, the support may be impregnated with a support modifier solution comprising a support modifier precursor and optionally one or more active metal precursors to form the modified support. After drying and calcination, the resulting modified support is impregnated with a second solution comprising precious metal precursor and optionally one or more of the active metal precursors, followed by drying and calcination to form the final catalyst.

In this embodiment, the support modifier solution may comprise a support modifier metal precursor and one or more active metal precursors, more preferably at least two active metal precursors. The precursors preferably are comprised of salts of the respective metals in solution, which, when heated, are converted to elemental metallic form or to a metal oxide. Since, in this embodiment, two or more active metal precursors are impregnated onto the support material simultaneously with the support modifier precursor, one or more of the resulting active metals may interact with the support modifier metal at a molecular metal upon formation to form one or more polymetallic crystalline species, such as cobalt tungstate. In other embodiments, one or more of the active metals will not interact with the support modifier metal precursor and are separately deposited on the support material, e.g., as discrete metal nanoparticles or as an amorphous metal mixture. Thus, the support material may be modified with one or more active metal precursors at the same time that it is modified with a support modifier metal, and the resulting active metals may or may not interact with the support modifier metal to form one or more polymetallic crystalline species.

In some embodiments, the support modifier may be added as particles to the support material. For example, one or more support modifier precursors, if desired, may be added to the support material by mixing the support modifier particles with the support material, preferably in water. When mixed it is preferred for some support modifiers to use a powdered material of the support modifiers, for example calcium metasilicate. If a powdered material is employed, the support modifier may be pelletized, crushed and sieved prior to being added to the support.

As indicated, in most embodiments, the support modifier preferably is added through a wet impregnation step. Preferably, a support modifier precursor to the support modifier may be used. Some exemplary support modifier precursors include alkali metal oxides, alkaline earth metal oxides, Group IIB metal oxides, Group IIIB metal oxides, Group IVB metal oxides, Group VB metal oxides, Group VIB metal oxides, Group VIIB metal oxides, and/or Group VIII metal oxides, as well as preferably aqueous salts thereof.

Although the overwhelming majority of metal oxides and polyoxoion salts are insoluble, or have a poorly defined or limited solution chemistry, the class of isopoly- and heteropolyoxoanions of the early transition elements forms an important exception. These complexes may be represented by the general formulae:

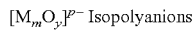  Isopolyanions

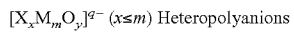 Heteropolyanions where M is selected from tungsten, molybdenum, vanadium, niobium, tantalum and mixtures thereof, in their highest ($d^0$, $d^1$) oxidations states. Such polyoxometalate anions form a structurally distinct class of complexes based predominately, although not exclusively, upon quasi-octahedrally-coordinated metal atoms. The elements that can function as the addenda atoms, M, in heteropoly- or isopolyanions may be limited to those with both a favorable combination of ionic radius and charge and the ability to form $d_\pi$-$p_\pi$ M-O bonds. There is little restriction, however, on the heteroatom, X, which may be selected from virtually any element other than the rare gases. See, e.g., M. T. Pope, *Heteropoly and Isopoly Oxonietalates*, Springer Verlag, Berlin, 1983, 180; Chapt. 38, *Comprehensive Coordination Chemistry*, Vol. 3, 1028-58, Pergamon Press, Oxford, 1987, the entireties of which are incorporated herein by reference.

Polyoxometalates (POMs) and their corresponding heteropoly acids (HPAs) have several advantages making them economically and environmentally attractive. First, HPAs have a very strong acidity approaching the superacid region, Bronsted acidity. In addition, they are efficient oxidants exhibiting fast reversible multielectron redox transformations under rather mild conditions. Solid HPAs also possess a discrete ionic structure, comprising fairly mobile basic structural units, e.g., heteropolyanions and countercations ($H^+$, $H_3O^+$, $H_5O_2^+$, etc.), unlike zeolites and metal oxides.

Preferably, the support modifier precursor comprises a POM, which preferably comprises a metal selected from the group consisting of tungsten, molybdenum, niobium, vanadium and tantalum. In some embodiments, the POM comprises a hetero-POM. A non-limiting list of suitable POMs includes ammonium metatungstate (($NH_4$)$_6$ $H_2W_{12}O_{40}$·$xH_2O$), ammonium heptamolybdate tetrahydrate (($NH_4$)$_6$$MO_7O_{24}$·$4H_2O$), silicotungstic acid hydrate ($H_4SiW_{12}O_{40}$·$H_2O$), phosphotungstic acid ($H_3PW_{12}O_{40}$·$nH_2O$), silicomolybdic acid ($H_4SiMo_{12}O_{40}$·$nH_2O$), phosphomolybdic acid ($H_3PMo_{12}O_{40}$·$nH_2O$) niobium oxalate hexahydrate ([Nb($HC_2O_4$)$_5$])·$6H_2O$), vanadium oxide ($V_2O_5$), ammonium vandate ($NH_4$)$VO_3$ and mixtures thereof. Especially preferred POMs include ammonium heptamolybdate tetrahydrate, silicomolybdic acid, phosphomolybdic acid, and vanadium oxide.

The use of POM-derived support modifiers in the catalyst compositions of the invention has now surprising and unexpectedly been shown to provide bi- or multi-functional catalyst functionality, desirably resulting in conversions for both acetic acid and byproduct esters such as ethyl acetate, thereby rendering them suitable for catalyzing mixed feeds comprising, for example, acetic acid and ethyl acetate.

Impregnation of the precious metal and one or more active metals onto the support, e.g., modified support, may occur simultaneously (co-impregnation) or sequentially. In simultaneous impregnation, the two or more metal precursors are mixed together and added to the support, preferably modified support, together followed by drying and calcination to form the final catalyst composition. With simultaneous impregnation, it may be desired to employ a dispersion agent, surfactant, or solubilizing agent, e.g., ammonium oxalate or an acid such as acetic or nitric acid, to facilitate the dispersing or solubilizing of the first, second and/or optional third metal precursors in the event the two precursors are incompatible with the desired solvent, e.g., water.

In sequential impregnation, the first metal precursor may be first added to the support followed by drying and calcining, and the resulting material may then be impregnated with the second metal precursor followed by an additional drying and calcining step to form the final catalyst composition. Additional metal precursors (e.g., a third metal precursor) may be added either with the first and/or second metal precursor or in a separate third impregnation step, followed by drying and calcination.

The use of a solvent, such as water, glacial acetic acid, a strong acid such as hydrochloric acid, nitric acid, or sulfuric acid, or an organic solvent, is preferred in the support modification step, e.g., for impregnating a support modifier precursor onto the support material. The support modifier solution comprises the solvent, preferably water, a support modifier precursor, and preferably one or more active metal precursors. The solution is stirred and combined with the support material using, for example, incipient wetness techniques in which the support modifier precursor is added to a support material having the same pore volume as the volume of the solution. Impregnation occurs by adding, optionally drop wise, a solution containing the precursors of either or both the support modifiers and/or active metals, to the dry support material. Capillary action then draws the support modifier into the pores of the support material. The thereby impregnated support can then be formed by drying, optionally under vacuum, to drive off solvents and any volatile components within the support mixture and depositing the support modifier on and/or within the support material. Drying may occur, for example, at a temperature from 50° C. to 300° C., e.g., from 50° C. to 200° C. or about 120° C., optionally for a period from 1 to 24 hours, e.g., from 3 to 15 hours or from 6 to 12 hours. The dried support may be calcined optionally with ramped heating, for example, at a temperature from 300° C. to 900° C., e.g., from 350° C. to 850° C., from 400° C. to 750° C., from 500° C. to 600° C. or at about 550° C., optionally for a period of time from 1 to 12 hours, e.g., from 2 to 10 hours, from 4 to 8 hours or about 6 hours, to form the final modified support. Upon heating and/or the application of vacuum, the metal(s) of the precursor(s) preferably decompose into their oxide or elemental form. In some cases, the completion of removal of the solvent may not take place until the catalyst is placed into use and/or calcined, e.g., subjected to the high temperatures encountered during operation. During the calcination step, or at least during the initial phase of use of the catalyst, such compounds are converted into a catalytically active form of the metal or a catalytically active oxide thereof.

Once formed, the modified calcined support may be shaped into particles having the desired size distribution, e.g., to form particles having an average particle size in the range from 0.2 to 0.4 cm. The supports may be extruded, pelletized, tabletized, pressed, crushed or sieved to the desired size distribution. Any of the known methods to shape the support materials into desired size distribution can be employed. Alternatively, support pellets may be used as the starting material used to make the modified support and, ultimately, the final catalyst.

In one embodiment, the precious metal and one or more active metals are impregnated onto the support, preferably onto any of the above-described modified supports. A precursor of the precious metal preferably is used in the metal impregnation step, such as a water soluble compound or water dispersible compound/complex that includes the precious metal of interest. Similarly, precursors to one or more active metals may also be impregnated into the support, preferably modified support. Depending on the metal precursors employed, the use of a solvent, such as water, glacial acetic acid, nitric acid or an organic solvent, may be preferred to help solubilize one or more of the metal precursors.

In one embodiment, separate solutions of the metal precursors are formed, which are subsequently blended prior to being impregnated on the support. For example, a first solution may be formed comprising a first metal precursor, and a second solution may be formed comprising the second metal precursor and optionally the third metal precursor. At least one of the first, second and optional third metal precursors preferably is a precious metal precursor, and the other(s) are preferably active metal precursors (which may or may not comprise precious metal precursors). Either or both solutions preferably comprise a solvent, such as water, glacial acetic acid, hydrochloric acid, nitric acid or an organic solvent.

In one exemplary embodiment, a first solution comprising a first metal halide is prepared. The first metal halide optionally comprises a tin halide, e.g., a tin chloride such as tin (II) chloride and/or tin (IV) chloride. Optionally, a second metal precursor, as a solid or as a separate solution, is combined with the first solution to form a combined solution. The second metal precursor, if used, preferably comprises a second metal oxalate, acetate, halide or nitrate, e.g., cobalt nitrate. The first metal precursor optionally comprises an active metal, optionally copper, iron, cobalt, nickel, chromium, molybdenum, tungsten, or tin, and the second metal precursor, if present, optionally comprises another active metal (also optionally copper, iron, cobalt, nickel, chromium, molybdenum, tungsten, or tin). A second solution is also prepared comprising a precious metal precursor, in this embodiment preferably a precious metal halide, such as a halide of rhodium, ruthenium, platinum or palladium. The second solution is combined with the first solution or the combined solution, depending on whether the second metal precursor is desired, to form a mixed metal precursor solution. The resulting mixed metal precursor solution may then be added to the support, optionally a modified support, followed by drying and calcining to form the final catalyst composition as described above. The resulting catalyst may or may not be washed after the final calcination step. Due to the difficulty in solubilizing some precursors, it may be desired to reduce the pH of the first and/or second solutions, for example by employing an acid such as acetic acid, hydrochloric acid or nitric acid, e.g., 8 M $HNO_3$.

In another aspect, a first solution comprising a first metal oxalate is prepared, such as an oxalate of copper, iron, cobalt, nickel, chromium, molybdenum, tungsten, or tin. In this embodiment, the first solution preferably further comprises an acid such as acetic acid, hydrochloric acid, phosphoric acid or nitric acid, e.g., 8 M $HNO_3$. Optionally, a second metal precursor, as a solid or as a separate solution, is combined with the first solution to form a combined solution. The second metal precursor, if used, preferably comprises a second metal oxalate, acetate, halide or nitrate, and preferably comprises an active metal, also optionally copper, iron, cobalt, nickel, chromium, molybdenum, tungsten, or tin. A second solution is also formed comprising a precious metal oxalate, for example, an oxalate of rhodium, ruthenium, platinum or palladium, and optionally further comprises an acid such as acetic acid, hydrochloric acid, phosphoric acid or nitric acid, e.g., 8 M $HNO_3$. The second solution is combined with the first solution or the combined solution, depending on whether the second metal precursor is desired, to form a mixed metal precursor solution. The resulting mixed metal precursor solution may then be added to the support, optionally a modified support, followed by drying and calcining to form the final catalyst composition as described above. The resulting catalyst may or may not be washed after the final calcination step.

In one embodiment, the impregnated support, optionally impregnated modified support, is dried at a temperature from 100° C. to 140° C., from 110° C. to 130° C., or about 120° C., optionally from 1 to 12 hours, e.g., from 2 to 10 hours, from 4 to 8 hours or about 6 hours. If calcination is desired, it is preferred that the calcination temperature employed in this step is less than the calcination temperature employed in the formation of the modified support, discussed above. The second calcination step, for example, may be conducted at a temperature that is at least 50° C., at least 100° C., at least 150° C. or at least 200° C. less than the first calcination step, i.e., the calcination step used to form the modified support. For example, the impregnated catalyst may be calcined at a temperature from 200° C. to 500° C., from 300° C. to 400° C., or about 350° C., optionally for a period from 1 to 12 hours, e.g., from 2 to 10 hours, from 4 to 8 hours or about 6 hours.

In one embodiment, ammonium oxalate is used to facilitate solubilizing of at least one of the metal precursors, e.g., a tin precursor, as described in US Pub. No. US2011/0190117A1, the entirety of which is incorporated herein by reference. In this aspect, the first metal precursor optionally comprises an oxalate of a precious metal, e.g., rhodium, palladium, or platinum, and a second metal precursor optionally comprises an oxalate tin. A third metal precursor, if desired, comprises a nitrate, halide, acetate or oxalate of chromium, copper, or cobalt. In this aspect, a solution of the second metal precursor may be made in the presence of ammonium oxalate as solubilizing agent, and the first metal precursor may be added thereto, optionally as a solid or a separate solution. If used, the third metal precursor may be combined with the solution comprising the first and second metal precursors, or may be combined with the second metal precursor, optionally as a solid or a separate solution, prior to addition of the first metal precursor. In other embodiments, an acid such as acetic acid, hydrochloric acid or nitric acid may be substituted for the ammonium oxalate to facilitate solubilizing of the tin oxalate. The resulting mixed metal precursor solution may then be added to the support, optionally a modified support, followed by drying and calcining to form the final catalyst composition as described above.

The specific precursors used in the various embodiments of the invention may vary widely. Suitable metal precursors may include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, sodium platinum chloride, and platinum ammonium nitrate, $Pt(NH_3)_4(NO_4)_2$. Generally, both from the point of view of economics and environmental aspects, aqueous solutions of soluble compounds of platinum and palladium are preferred. In one embodiment, the first metal precursor is not a metal halide and is substantially free of metal halides. Without being bound to theory, such non-(metal halide) precursors are believed to increase selectivity to ethanol. A particularly preferred precursor to platinum is platinum ammonium nitrate, $Pt(NH_3)_4(NO_4)_2$. Calcining of the solution with the support and active metal may occur, for example, at a temperature from 250° C. to 800° C., e.g., from 300 to 700° C. or about 500° C., optionally for a period from 1 to 12 hours, e.g., from 2 to 10 hours, from 4 to 8 hours or about 6 hours.

In one aspect, the "promoter" metals or metal precursors are first added to the support, followed by the "main" or "primary" metals or metal precursors. Of course the reverse order of addition is also possible. Exemplary precursors for promoter metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of two active metals, e.g., Pt and Sn.

As an example, PtSnCo/WO₃ on SiO₂ may be prepared by first impregnating a precursor to WO₃, preferably a POM precursor to WO₃, on the SiO₂, followed by the co-impregnation with platinum oxalate, tin oxalate, and cobalt nitrate, preferably in the presence of an acid such as acetic acid, hydrochloric acid or nitric acid. Again, each impregnation step may be followed by drying and calcination steps, with the second calcination temperature preferably being less than the first calcination temperature. In another example, the second and third metals are co-impregnated with the precursor to WO₃ on the support, optionally forming a mixed oxide with WO₃, e.g., cobalt tungstate, followed by drying and calcination. The resulting modified support may be impregnated, preferably in a single impregnation step, with one or more of the first, second and third metals, followed by a second drying and calcination step. In this manner, cobalt tungstate may be formed on the modified support. Again, the temperature of the second calcining step preferably is less than the temperature of the first calcining step.

Use of Catalyst to Hydrogenate Acetic Acid

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment the invention is to a process for producing ethanol by hydrogenating a feedstock comprising compounds selected from acetic acid, ethyl acetate and mixtures thereof in the presence of any of the above-described catalysts. One particular preferred reaction is to make ethanol from acetic acid. The hydrogenation reaction may be represented as follows:

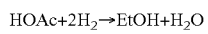

$$HOAc + 2H_2 \rightarrow EtOH + H_2O$$

In some embodiments, the catalyst may be characterized as a multifunctional catalyst in that it effectively catalyzes the hydrogenation of acetic acid to ethanol as well as the conversion of ethyl acetate to one or more products, preferably ethanol. A multifunctional catalyst, under steady state conditions, may be not produce ethyl acetate, but rather consumes ethyl acetate recycles at a rate is substantially equal to the rate of ethyl acetate formation in the reactor.

The raw materials, acetic acid and hydrogen, fed to the hydrogenation reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507, 562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, the feedstock comprises acetic acid and ethyl acetate. A suitable acetic acid feed stream comprises one or more of the compounds selected from the group consisting of acetic acid, acetic anhydride, acetaldehyde, ethyl acetate, diethyl acetal, diethyl ether, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles. In some embodiments, multiple catalyst beds are employed in the same reactor or in different reactors, e.g., in series. For example, in one embodiment, a first catalyst functions in a first catalyst stage as a catalyst for the hydrogenation of an alkanoic acid, e.g., acetic acid, to its corresponding alcohol, e.g., ethanol, and a second multifunctional catalyst is employed in the second stage for converting unreacted acetic acid to ethanol as well as converting byproduct ester, e.g., ethyl acetate, to additional products, preferably to ethanol. The catalysts of the invention may be employed in either or both the first and/or second stages of such reaction systems.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2000 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1. For a mixed feedstock, the molar ratio of hydrogen to ethyl acetate may be greater than 5:1, e.g., greater than 10:1 or greater than 15:1.

Contact or residence time can also vary widely, depending upon such variables as amount of feedstock (acetic acid and/or ethyl acetate), catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In particular, by employing the catalysts of the invention, the hydrogenation of acetic acid and/or ethyl acetate may achieve favorable conversion and favorable selectivity and productivity to ethanol in the reactor. For purposes of the present invention, the term "conversion" refers to the net change of the flow of acetic acid or ethyl acetate into the reactor as compared to the flow of acetic acid or ethyl acetate out of the reactor. Conversion is expressed as a percentage based on acetic acid or ethyl acetate in the feed. The acetic acid conversion may be at least 20%, more preferably at least 30%, at least 60%, at least 75%, at least 80%, at least 90%, at least 95% or at least 99%.

During the hydrogenation of acetic acid, diethyl ether may be produced as a byproduct. The problem with this ether product is that it is difficult to recycle back to the reactor and hydrogenate to a useful product, due to the relative stability of the ether. For every mole of ether formed, two moles of potential ethanol product are lost. However, the preferred catalysts of the invention minimize the formation of diethyl ether during the hydrogenation of acetic acid, without hindering the hydrogenation. Employing such catalysts for the hydrogenation process, the selectivity to diethyl ether may be less than 0.25%, less than 0.2%, less than 0.1%, or less than 0.05%.

Also during the hydrogenation of acetic acid, ethyl acetate may be produced as a byproduct. Without consuming any ethyl acetate from the mixed vapor phase reactants, the conversion of ethyl acetate would be deemed negative. A catalyst having a negative conversion may result in the undesirable build up of ethyl acetate in the system, particularly for systems employing one or more recycle streams to the reactor.

Certain catalysts of the invention, however, are multifunctional in that they effectively catalyze the conversion of acetic acid to ethanol as well as the conversion of an alkyl acetate such as ethyl acetate to one or more products other than that alkyl acetate. A multifunctional catalyst is preferably effective for consuming ethyl acetate at a rate sufficiently great so as to at least offset the rate of ethyl acetate production, thereby resulting in a non-negative ethyl acetate conversion, i.e., no net increase in ethyl acetate is realized. The use of such catalysts may result, for example, in an ethyl acetate conversion that is effectively 0% or that is greater than 0%. In some embodiments, the catalysts of the invention, on a per pass, are effective in providing ethyl acetate conversions of at least 5%, e.g., at least 10%, at least 15%, at least 20%, or at least 35%.

In continuous processes, the ethyl acetate being added (e.g., recycled) to the hydrogenation reactor and ethyl acetate leaving the reactor in the crude product preferably approaches a certain level after the process reaches equilibrium. The use of a multifunctional catalyst that catalyzes the conversion of ethyl acetate as well as acetic acid results in a lower amount of ethyl acetate added to the reactor and less ethyl acetate produced. In preferred embodiments, the concentration of ethyl acetate in the mixed feed and crude product is less than 40 wt. %, less than 25 wt. % or less than 15 wt. % after equilibrium has been achieved. In preferred embodiments, the process forms a crude product comprising ethanol and ethyl acetate, and the crude product has an ethyl acetate steady state concentration from 0.1 to 40 wt %, e.g., from 0.1 to 20 wt % or from 0.1 to 10 wt %.

Although catalysts that have high acetic acid conversions are desirable, such as at least 60%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid and/or ethyl acetate. It should be understood that each compound converted from acetic acid and/or ethyl acetate has an independent selectivity and that selectivity is independent of conversion. For example, if 60 mole % of the converted acetic acid is converted to ethanol, we refer to the ethanol selectivity as 60%. For purposes of the present invention, the total selectivity is based on the combined converted acetic acid and ethyl acetate. Preferably, total selectivity to ethanol is at least 60%, e.g., at least 70%, or at least 80%, at least 85% or at least 88%. Preferred embodiments of the hydrogenation process also have low selectivity to undesirable products, such as methane, ethane, carbon dioxide, and diethyl ether (as discussed). The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

| CRUDE ETHANOL PRODUCT COMPOSITIONS | | | | |
|---|---|---|---|---|
| Component | Conc. (wt. %) | Conc. (wt. %) | Conc. (wt. %) | Conc. (wt. %) |
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 0 to 25 | 1 to 20 | 3 to 15 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.1 wt. % to 15 wt. %, from 0.1 wt. % to 10 wt. % or from 0.1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%. Also, the conversion of ethyl acetate may be greater than 0%, preferably greater than 5%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 96 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The following examples describe the catalyst and process of this invention.

EXAMPLES

I. Examples 1-8

Eight Platinum/tin/cobalt catalysts were prepared in Examples 1-8 using different support modifiers. The resulting catalysts were then tested in a hydrogenation unit with a mixed feedstock. The catalyst compositions for Example 1-8 are provided in Table 2.

TABLE 2

| Example | Catalyst |
|---|---|
| 1 | $SiO_2$—$WO_3$(12)—Pt(1)—Co(4.8)—Sn(4.1) |
| 2 | $SiO_2$—Si(1/12)$WO_3$(12)—Pt(1)—Co(4.8)—Sn(4.1) |
| 3 | $SiO_2$—P(1/12)$WO_3$(12)—Pt(1)—Co(4.8)Sn(4.1) |
| 4 | $SiO_2$—$MoO_3$(7.4)—Pt(1)—Co(4.8)—Sn(4.1) |
| 5 | $SiO_2$—Si(1/12)$MoO_3$(7.4)—Pt(1)—Co(4.8)—Sn(4.1) |
| 6 | $SiO_2$—P(1/12)$MoO_3$(7.4)—Pt(1)—Co(4.8)—Sn(4.1) |
| 7 | $SiO_2$—$Nb_2O_5$(7.4)—Pt(1)—Co(4.8)—Sn(4.1) |
| 8 | $SiO_2$—$V_2O_5$(4.8)—Pt(1)—Co(4.8)—Sn(4.1) |

Catalyst Preparation Overview.

A high surface area (HSA) commercial $SiO_2$ support (HSA SS #61138, 3 mm pellets, NorPro) was used as starting material for the transition metal oxide modified supports. In general, the catalyst supports were prepared by impregnating the $SiO_2$ extrudates with an aqueous solution of the corresponding W, Mo, Nb, or V polyoxometalate (POM) precursor (see Experimental Section), which was followed by drying at 120° C., and calcination at 550° C. under air. The metal-supported catalysts were carried out as single-step incipient wetness impregnations using an aqueous solution of Sn, Co, and Pt in diluted nitric acid and the metal-oxide modified silica support.

The [$SiO_2$-$MO_x$(n)] catalyst supports (M=W, Mo, Nb, V) were prepared using equal molar amounts with respect to the early transition metal M. Hence the corresponding oxide amount, n, in wt % is provided in parentheses. The individual catalyst and support preparations are described in detail in the Experimental Section. A summary of the catalyst preparation protocol is provided in FIG. 1. The catalytic activities of the corresponding {PtCoSn}-supported catalysts are summarized in Table 3.

Experimental.

Materials. Metal precursors, tin(II) oxalate, $SnS_2O_4$, and cobalt(II) nitrate hexahydrate, $Co(NO_3)_2 \cdot 6H_2O$, were purchased from Aldrich and used without further purification. Ammonium metatungstate, $(NH_4)_6H_2W_{12}O_{40} \cdot H_2O$ (AMT), ammonium heptamolybdate tetrahydrate, $(NH_4)_6Mo_7O_{24} \cdot 4H_2O$ (AHM), silicotungstic acid hydrate, $H_4SiW_{12}O_{40} \cdot H_2O$ (HSiW$_{12}$), phosphotungstic acid, $H_3PW_{12}O_{40} \cdot nH_2O$ (H—PW$_{12}$), silicomolybdic acid, $H_4SiMo_{12}O_{40} \cdot nH_2O$ (H—SiMo$_{12}$), phosphomolybdic acid, $H_3PMo_{12}O_{40} \cdot nH_2O$ (H-PMo$_{12}$), niobium oxalate hexahydrate, [Nb(HC$_2$O$_4$)$_5$]$\cdot$6H$_2$O (NbOX), and vanadium (V) oxide, $V_2O_5$ were obtained from Aldrich. Platinum (II) oxalate solution, $PtC_2O_4$, (~10 wt % Pt) was obtained from Heraeus and used as received. Silica catalyst supports (HSA SS #61138, SA=250 m²/g; 3 mm pellets; $SiO_2$, were used as received from a vendor. Acetic acid and nitric acid were obtained from Fisher Scientific.

Analytical Procedures (Organic Products).

The reactor effluent was periodically collected, and product analysis was carried out using an authentic sample calibrated GC off-line analysis method. Temperature program: $T_{init}$=60° C. (hold 2.5 min); ramp (20 deg/min) to 245° C. (hold 5.5 min). Total run time 17.25 min (Oven maximum temperature 280° C.).

Catalyst Preparations.

The commercial $SiO_2$ support (HSA SS #61138) was used as 3 mm pellets unless mentioned otherwise. In general, the modified supports were prepared by impregnating the $SiO_2$ extrudates with an aqueous solution of the corresponding W, Mo, Nb, or V precursor, followed by drying at 120° C., and calcination at 550° C. under air. The catalyst preparations were carried out as single-step incipient wetness impregnations using an aqueous solution of Sn, Co, and Pt in diluted nitric acid and the modified silica support.

The [$SiO_2$-$MO_x(n)$] catalyst supports (M=W, Mo, Nb, V) were prepared maintaining the same molar amounts of M, hence the corresponding oxide amount, n, in wt % is provided in parentheses. The individual catalyst and support preparations are described in detail in the following Section. The catalytic activities of the {PtCoSn}-supported catalysts are summarized in Table 1.

Example 1

$SiO_2$—$WO_3(12)$

For this preparation, 176.0 g of the $SiO_2$ support (NorPro, 3 mm pellets) was used. The aqueous impregnation solution was prepared by dissolving 25.504 g (8.63 mmol) of ammonium metatungstate hydrate (AMT) in 250 mL of deionized $H_2O$. The support was then impregnated using incipient wetness technique, and the material was dried using a rotor evaporator, followed by drying at 120° C. overnight under circulating air. The dried material was then calcined at 550° C./air for six hours. Yield: ~200 g of light yellow extrudates. The precious and active metals were then impregnated onto the modified support according to the Catalyst Preparation procedure described below.

Example 2

$SiO_2$—$Si(1/12)WO_3(12)$

For this preparation, 22.0 g of the $SiO_2$ support (NorPro, 3 mm pellets) was used. The aqueous impregnation solution was prepared by dissolving 3.104 g (1.08 mmol) of silicotungstic acid hydrate in 32 ml of deionized $H_2O$. The support was then impregnated using incipient wetness technique, and the material was dried using a rotor evaporator, followed by drying at 120° C. overnight under circulating air. The dried material was then calcined at 550° C./air for six hours. Yield: ~25 g of light yellow extrudates. The precious and active metals were then impregnated onto the modified support according to the Catalyst Preparation procedure described below.

Example 3

$SiO_2$—$P(1/12)WO_3(12)$

For this preparation, 22.0 g of the $SiO_2$ support (NorPro, 3 mm pellets) was used. The aqueous impregnation solution was prepared by dissolving 3.106 g (1.08 mmol) of phosphotungstic acid hydrate in 32 ml of deionized $H_2O$. The support was then impregnated using incipient wetness technique, and the material was dried using a rotor evaporator, followed by drying at 120° C. overnight under circulating air. The dried material was then calcined at 550° C./air for six hours. Yield: ~25 g of light yellow extrudates. The precious and active metals were then impregnated onto the modified support according to the Catalyst Preparation procedure described below.

Example 4

$SiO_2$—$MoO_3(7.4)$

For this preparation, 23.14 g of the $SiO_2$ support (NorPro, 3 mm pellets) was used. The aqueous impregnation solution was prepared by dissolving 2.284 g (1.85 mmol) of ammonium heptamolybdate tetrahydrate in 33.5 ml of deionized $H_2O$. The support was then impregnated using incipient wetness technique, and the material was dried using a rotor evaporator, followed by drying at 120° C. overnight under circulating air. The dried material was then calcined at 550° C./air for six hours. Yield: ~25 g of yellow extrudates. The precious and active metals were then impregnated onto the modified support according to the Catalyst Preparation procedure described below.

Example 5

$SiO_2$—$Si(1/12)MoO_3(7.4)$

For this preparation, 23.14 g of the $SiO_2$ support (NorPro, 3 mm pellets) was used. The aqueous impregnation solution was prepared by dissolving 1.996 g (1.09 mmol) of silicomolybdic acid hydrate in 33.5 ml of deionized $H_2O$. The support was then impregnated using incipient wetness technique, and the material was dried using a rotor evaporator, followed by drying at 120° C. overnight under circulating air. The dried material was then calcined at 550° C./air for six hours. Yield: ~25 g of yellow extrudates. The precious and active metals were then impregnated onto the modified support according to the Catalyst Preparation procedure described below.

Example 6

$SiO_2$—$P(1/12)MoO_3(7.4)$

For this preparation, 23.14 g of the $SiO_2$ support (NorPro, 3 mm pellets) was used. The aqueous impregnation solution was prepared by dissolving 1.968 g (1.09 mmol) of phosphomolybdic acid in 33.5 ml of deionized $H_2O$. The support was then impregnated using incipient wetness technique, and the material was dried using a rotor evaporator, followed by drying at 120° C. overnight under circulating air. The dried material was then calcined at 550° C./air for six hours. Yield: ~25 g of yellow extrudates. The precious and active metals were then impregnated onto the modified support according to the Catalyst Preparation procedure described below.

Example 7

$SiO_2$—$Nb_2O_5(6.9)$

For this preparation, 23.28 g of the $SiO_2$ support (NorPro, 3 mm pellets) was used. The aqueous impregnation solution was prepared by dissolving 3.921 g (6.07 mol) of niobium(V) oxalate hexahydrate in 34 ml of deionized $H_2O$. The support was then impregnated using incipient wetness technique, and the material was dried using a rotor evaporator, followed by drying at 120° C. overnight under circulating air. The dried material was then calcined at 550° C./air for six hours. Yield: ~25 g of white extrudates. The precious and active metals were then impregnated onto the modified support according to the Catalyst Preparation procedure described below.

Example 8

SiO$_2$—V$_2$O$_5$(4.8)

For this preparation, 23.14 g of the SiO$_2$ support (NorPro, 3 mm pellets) was used. The aqueous impregnation solution was prepared by first suspending 1.177 g (6.47 mmol) of vanadium (V) oxide in 30 ml of deionized H$_2$O. Next, 2.0 ml of aqueous ammonia (30 wt %) were added and the oxide was dissolved with stirring at room temperature. The support was then impregnated with this solution using incipient wetness technique, and the material was dried using a rotor evaporator, followed by drying at 120° C. overnight under circulating air. The dried material was then calcined at 550° C./air for six hours. Yield: ~25 g of yellow-orange extrudates. The precious and active metals were then impregnated onto the modified support according to the Catalyst Preparation procedure described below.

Catalyst Preparation. [SiO$_2$-MO$_x$(n)]-Pt(1.0)-Co(4.8)-Sn(4.1); M=W, Mo, Nb, V.

Catalyst preparations for Examples 1-8 were carried out using the following general procedure and 9.775 g of each of the modified silica supports from Examples 1-8. The metal impregnation solution was prepared as follows. First, 3.5 ml of 8 M HNO$_3$ was added to a glass vial containing a Teflon coated stir bar. Next, 0.7770 g (3.76 mmol) of solid tin (II) oxalate was slowly added with stirring. The solution was then diluted by adding 2.5 ml of deionized H$_2$O, and 2.5530 g (8.77 mmol) of solid cobalt (II) nitrate hexahydrate was added with stirring. Separately, 1.1673 g of PtC$_2$O$_4$ solution (10.12 wt % Pt) was diluted to a total volume of 2.0 ml by adding deionized H$_2$O. The diluted platinum solution was then added to the solution containing tin and cobalt, and the mixture was stirred for another 5 min at room temperature. The [SiO$_2$-(MO$_x$)] support was then impregnated using incipient wetness techniques, the material was then dried using a rotor evaporator, and dried further at 120° C. overnight under moving air. The final material was then calcined at 350° C. under flowing air for six hours. Yield: ~10 g of finished catalyst (dark/black extrudates).

II. Comparative Examples 9-10

Catalyst Preparations

Example 9

SiO$_2$—W(10)-Re(5)-Ru(1)

The catalyst was prepared by impregnating a pre-shaped silica support (3 mm pellets, SA=250 m$^2$/g; NorPro Saint Gobain) with an aqueous solution containing the precursors for W, Re, and Ru in a soluble form. The actual catalyst was prepared as follows. The aqueous impregnation solution was prepared by adding 3.351 g of ammonium metatungstate, and 1.8007 g of ammonium perrhenate to 20 mL of H$_2$O. The solution was heated to 50° C., and stirred for 5 min at this temperature. Next, 0.7774 g of Ruthenium nitrosylnitrate were added and dissolved with stirring. The solution was then added to 21 g of the silica support (incipient wetness technique), and the material was dried by rotor evaporation following by drying at 120° C. under air. The dried material was finally calcined at 500° C. under flowing air.

Example 10

SiO$_2$—W(10)-Re(5)-Rh(1)

The catalyst was prepared by impregnating a pre-shaped silica support (3 mm pellets, SA=250 m$^2$/g; NorPro Saint Gobain) with an aqueous solution containing the precursors for W, Re, and Ru in a soluble form. The actual catalyst was prepared as follows. The aqueous impregnation solution was prepared by adding 3.351 g of ammonium metatungstate, and 1.8007 g of ammonium perrhenate to 20 mL of H$_2$O. The solution was heated to 50° C., and stirred for 5 min at this temperature. Next, 0.6458 g of Rhodium (III) chloride hydrate were added and dissolved with stirring. The solution was then added to 21 g of the silica support (incipient wetness technique), and the material was dried by rotor evaporation following by drying at 120° C. under air. The dried material was finally calcined at 500° C. under flowing air.

Both catalysts for Example 9 and 10 were pretreated, and tested at the same conditions employed for Examples 1-8. The highest conversion of acetic acid was seen for the Ru-containing catalyst. This material also exhibited a high conversion of ethyl acetate. However, the selectivities toward ethanol are low, and a mixture of various hydrocarbons are the main reaction products.

Reactor System and Catalytic Testing Conditions.

The test unit comprised four independent tubular fixed bed reactor systems with common temperature control, pressure and gas and liquid feeds. The reactors were made of ⅜ inch (0.95 cm) 316 SS tubing, and were 12⅛ inches (30.8 cm) in length. The vaporizers were made of ⅜ inch (0.95 cm) 316 SS tubing and were 12⅜ inches (31.45 cm) in length. The reactors, vaporizers, and their respective effluent transfer lines were electrically heated (heat tape).

The reactor effluents were routed to chilled water condensers and knock-out pots. Condensed liquids were collected automatically, and then manually drained from the knock-out pots as needed. Non-condensed gases were passed through a manual back pressure regulator (BPR) and then scrubbed through water and vented to the fume hood. For each Example, 15 ml of catalyst (3 mm pellets) was loaded into reactor. Both inlet and outlet of the reactor were filled with glass beads (3 mm) to form the fixed bed. The following running conditions for catalyst screening were used: T=275° C., P=300 psig (2068 kPag), [Feed]=0.138 ml/min (pump rate), and [H$_2$]=513 sccm, gas-hourly space velocity (GHSV)= 2246 hr$^{-1}$. The mixed feed composition used for testing are summarized in the Table 3.

TABLE 3

| Mixed Feed Composition for Catalyst Performance Evaluation | | | | | |
|---|---|---|---|---|---|
| H$_2$O (wt. %) | Acetaldehyde (wt. %) | Ethanol (wt. %) | Ethyl Acetate (wt. %) | Acetic Acid (wt. %) | Diethyl Acetal (wt. %) |
| 0.65 | 0.55 | 5.70 | 20.72 | 69.92 | 2.45 |

Catalytic Results. The catalytic performance of [SiO$_2$-MO$_x$(n)]-Pt(1)-Co(4.8)-Sn(4.1) (M=W, Mo, Nb, V) and the comparative examples 9 and 10 was studied using a test unit consisting of four independent tubular fixed bed reactors, as described above, with common temperature control, pressure and gas and liquid feeds. The condensed liquids were collected automatically and then manually drained from the knock-out pots as needed, and analyzed by authentic-sample calibrated GC.

Acetic Acid Conversion and Ethanol Selectivity.

Figure 2:
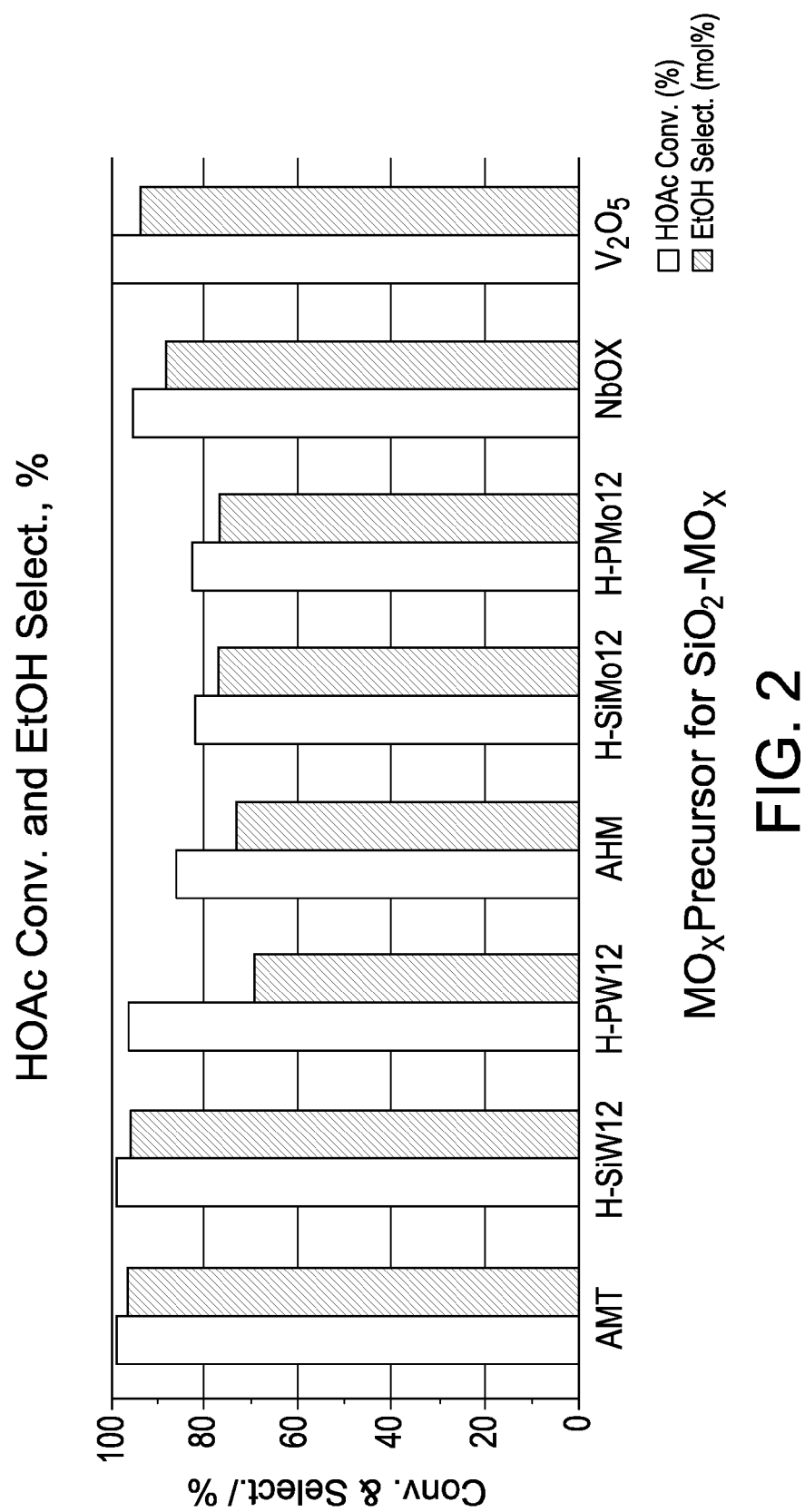
FIG. 2 is a graph showing conversion and selectivity for ethanol for various exemplary catalysts according to several embodiments of the present invention.

All eight materials in Examples 1-8 showed acetic acid conversions of 80% and greater. The highest conversions (>99%) were observed for the two tungsten-modified supports (AMT, H—SiW$_{12}$), and also for the vanadium oxide (V$_2$O$_5$) modified material. High ethanol selectivities were also observed for all three materials. Hence all three materials gave raise to ethanol selectivities of greater than 90%. Catalytic performance of materials obtained from AMT and H—SiW$_{12}$ were almost identical. Comparative examples 9 and 10 gave low ethanol selectivity and low acetic acid conversion, respectively. The catalytic results for acetic acid conversion and ethanol selectivity are summarized in FIG. 2 and Table 4. Catalysts from Examples 1, 2 and 8 surprisingly and unexpectedly showed net reductions in ethyl acetate indicating that the catalysts are multifunctional for converting both acetic acid and ethyl acetate.

TABLE 4

Summary of [SiO$_2$—MO$_x$(n)]—Pt(1)—Co(4.8)—Sn(4.1) (M = W, Mo, Nb, V)
Catalyst Performance Data Obtained Under Mixed Feed Conditions

| Ex. | Precursor | Support | HOAc Conv. (%) | EtOAc Conv. (%) | EtOH Select. (mol %) | EtOH Prod. (g/kg/h) | Product GC (wt. %) | | |
|---|---|---|---|---|---|---|---|---|---|
| | | | | | | | EtOH | EtOAc | Et$_2$O |
| 1 | AMT | SiO$_2$WO$_3$(12) | 99.4 | 23.7 | 97.1 | 626.2 | 61.5 | 15.6 | 0.2 |
| 2 | H—SiW$_{12}$ | SiO$_2$Si$_{1/2}$WO$_3$(12) | 99.4 | 24.8 | 96.3 | 626.9 | 61.3 | 15.1 | 0.1 |
| 3 | H—PW$_{12}$ | SiO$_2$P$_{1/12}$WO$_3$(12) | 96.8 | −65.9 | 69.7 | 385.3 | 41.4 | 33.4 | 0.1 |
| 4 | AHM | SiO$_2$MoO$_3$(7.4) | 86.5 | −57.6 | 73.7 | 360.7 | 39.4 | 31.7 | 0.01 |
| 5 | H—SiMo$_{12}$ | SiO$_2$Si$_{1/12}$MoO$_3$(7.4) | 82.5 | −35.5 | 77.2 | 373.9 | 39.5 | 28.4 | 0.01 |
| 6 | H—PMo$_{12}$ | SiO$_2$P$_{1/12}$MoO$_3$(7.4) | 82.5 | −34.5 | 77.3 | 382.7 | 39.8 | 28.1 | 0.02 |
| 7 | NbOX | SiO$_2$—Nb$_2$O$_5$(6.9) | 95.2 | −13.5 | 88.4 | 505.4 | 50.2 | 22.8 | 0.2 |
| 8 | V$_2$O$_5$ | SiO$_2$V$_2$O$_5$(4.8) | 99.4 | 1.3 | 93.7 | 591.1 | 56.0 | 20.6 | 0.02 |
| Comparative: Re(5)—Ru(1) | | | | | | | | | |
| 9 | AMT | SiO$_2$—WO$_3$(10) | 97.3 | 85.7 | −6.9 | −53.9 | 0.8 | 2.9 | 0.003 |
| Comparative: Re(5)—Rh(1) | | | | | | | | | |
| 10 | AMT | SiO$_2$—WO$_3$(10) | 16.6 | −25.4 | 63.9 | 163.9 | 11.3 | 25.8 | 0.05 |

Ethanol Productivity.

Figure 3:
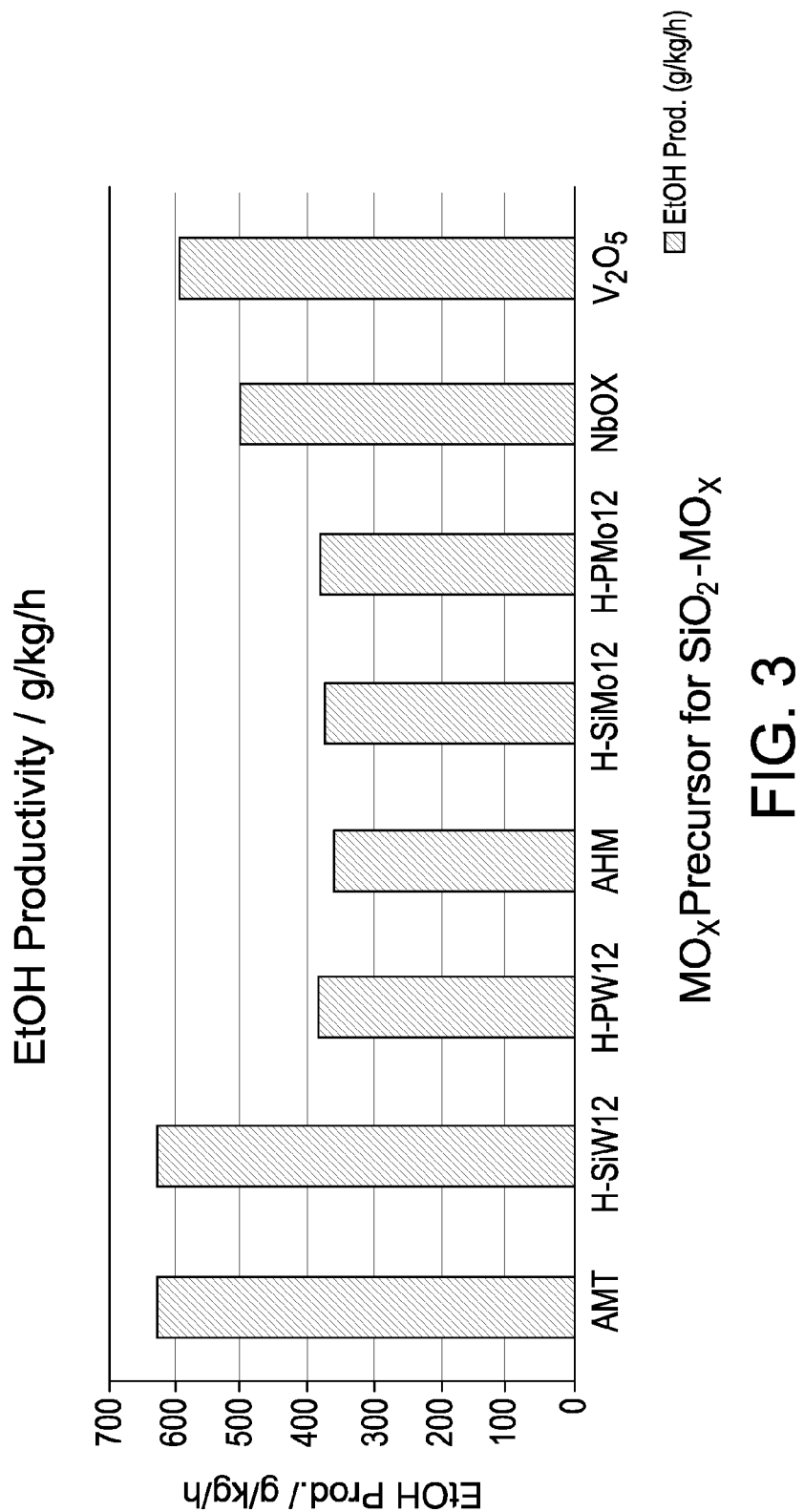
FIG. 3 is a graph showing ethanol productivity for various exemplary catalysts according to several embodiments of the present invention.

Both tungsten-modified materials exhibited ethanol productivities of more than 600 g/kg/h, and the vanadium-promoted support also gave a productivity of close to that value. All other material showed significantly lower productivities, mainly due to the lower selectivities towards ethanol (see FIG. 2). Again, the productivities seen for the catalysts prepared using the AMT and H—SiW$_{12}$ precursors are almost identical, emphasizing the similarity of the resulting support material. Comparative Example 9 gave low ethanol productivity. The catalytic results with respect to the ethanol productivity are summarized in FIG. 3.

Ethyl Acetate Conversion.

To maximize ethanol production in the hydrogenation of acetic acid, it is desirable to minimize ethyl acetate production. A significant and stable conversion of ethyl acetate, sustained over the life time of the catalyst, is desired in order to avoid build-up of the co-product in the recycle loop. Hydrogenolysis of ethyl acetate provides two moles of ethanol for each mole of ethyl acetate hydrogenated. This will further increase ethanol selectivity and the efficiency of the overall process.

Figure 4:
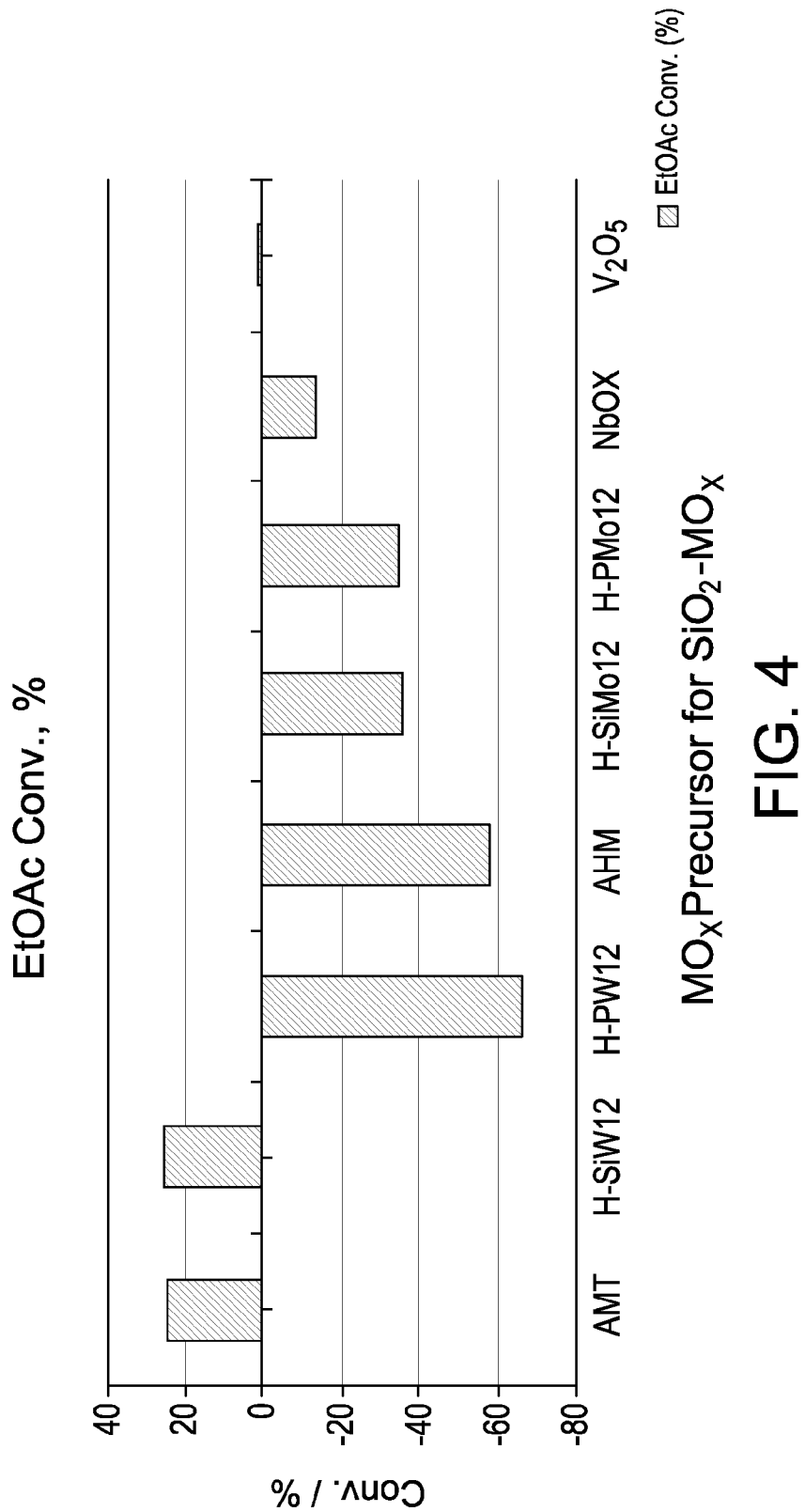
FIG. 4 is a graph showing ethyl acetate conversion for various exemplary catalysts according to several embodiments of the present invention.

In order to study the combined catalytic conversion of acetic acid and ethyl acetate, a product mixture according to Table 2 was used as the reactor feed. Out of the eight materials studied, three showed ethyl acetate conversion, indicated by the positive values in FIG. 4 (a negative value indicates increase in ethyl acetate production). Both the tungsten- and the vanadium-modified supports gave rise to net-ethyl acetate consumption. The three materials surprisingly and unexpectedly provided functionality for both acetic acid and ethyl acetate. Comparative example 10 gave low ethyl acetate conversion. The catalytic data with respect to ethyl acetate conversion is summarized in FIG. 4.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for producing ethanol comprising the steps of:
    passing a gaseous stream comprising hydrogen and an alkanoic acid in the vapor phase over a hydrogenation catalyst to form a product comprising an alcohol and less than about 0.25% ether based on the total weight of the product, wherein the hydrogenation catalyst is produced by the process comprising the steps of:
    impregnating a support modifier from ammonium metatungstate, ammonium heptamolybdate tetrahydrate, silicotungstic acid hydrate, phosphotungstic acid, silicomolybdic acid, phosphomolybdic acid, niobium oxalate hexahydrate, or vanadium oxide on a support to form a first impregnated support;
    calcining the first impregnated support to form a calcined support;
    impregnating one or more active metals from one or more metal precursors on the calcined support to form a second impregnated support, wherein the one or more active metals are selected from the group consisting of iron, cobalt, nickel, ruthenium, rhodium, platinum, palladium, osmium, iridium, titanium, zinc, chromium, molybdenum, tungsten, tin, lanthanum, cerium, manganese, and gold; and calcining the second impregnated support to form the catalyst.

2. The process of claim 1, wherein the alkanoic acid is acetic acid.

3. The process of claim 2, wherein the conversion of acetic acid is at least about 80%.

4. The process of claim 1, wherein acetic acid conversion is greater than 30%.

5. The process of claim 1, wherein the support modifier is present in an amount from 0.1 to 50 wt. %, based on the total weight of the catalyst composition.

6. The process of claim 1, wherein the support material is present in an amount from 25 to 99 wt. %, based on the total weight of the catalyst composition.

7. The process of claim 1, wherein the support material is selected from the group consisting of silica, alumina, titania, silica/alumina, calcium metasilicate, pyrogenic silica, high purity silica, zirconia, zeolites, carbon, or mixtures thereof.

8. The process of claim 1, wherein the one or more active metals is selected from the group consisting of palladium, iron, cobalt, platinum, tin and combinations thereof.

9. The process of claim 1, wherein the hydrogenation conditions include a pressure of 10 kPa to 3000 kPa and a hydrogen to acetic acid molar ratio of greater than 2:1.

10. A process for producing ethanol comprising the steps of:
passing a gaseous stream comprising hydrogen and an alkanoic acid in the vapor phase over a hydrogenation catalyst to form a product comprising an alcohol and substantially no ether, wherein the hydrogenation catalyst is produced by the process comprising the steps of:
impregnating a support modifier from ammonium heptamolybdate tetrahydrate, silicomolybdic acid, phosphomolybdic acid, or vanadium oxide on a support to form a first impregnated support;
calcining the first impregnated support to form a calcined support;
impregnating one or more active metals from one or more metal precursors on the calcined support to form a second impregnated support, wherein the one or more active metals are selected from the group consisting of iron, cobalt, nickel, ruthenium, rhodium, platinum, palladium, osmium, iridium, titanium, zinc, chromium, molybdenum, tungsten, tin, lanthanum, cerium, manganese, and gold; and
calcining the second impregnated support to form the catalyst.

11. The process of claim 10, wherein the alkanoic acid is acetic acid.

12. The process of claim 11, wherein the conversion of acetic acid to ethanol is at least about 80%.

13. The process of claim 11, wherein acetic acid conversion is greater than 30%.

14. The process of claim 11, wherein the support modifier is present in an amount from 0.1 to 50 wt. %, based on the total weight of the catalyst composition.

15. The process of claim 11, wherein the support material is present in an amount from 25 to 99 wt. %, based on the total weight of the catalyst composition.

16. The process of claim 11, wherein the support material is selected from the group consisting of silica, alumina, titania, silica/alumina, calcium metasilicate, pyrogenic silica, high purity silica, zirconia, zeolites, carbon, or mixtures thereof.

17. The process of claim 11, wherein the one or more active metals is selected from the group consisting of palladium, iron, cobalt, platinum, tin and combinations thereof.

18. The process of claim 11, wherein the hydrogenation conditions include a pressure of 10 kPa to 3000 kPa and a hydrogen to acetic acid molar ratio of greater than 2:1.

* * * * *